US00PP21755P2

(12) United States Plant Patent
Eveleens

(10) Patent No.: US PP21,755 P2
(45) Date of Patent: Mar. 1, 2011

(54) ***GERBERA* PLANT NAMED 'REDWOOD'**

(50) Latin Name: *Gerbera jamesonii*
Varietal Denomination: Redwood

(75) Inventor: Jan Leendert Eveleens, Aalsmeer (NL)

(73) Assignee: Florist de Kwakel B.V., Aalsmeer (NL)

( * ) Notice: Subject to any disclaimer, the term of this patent is extended or adjusted under 35 U.S.C. 154(b) by 0 days.

(21) Appl. No.: 12/586,402

(22) Filed: Sep. 21, 2009

(51) Int. Cl.
*A01H 5/00* (2006.01)

(52) U.S. Cl. ..... Plt./357
(58) Field of Classification Search ..... Plt./357
See application file for complete search history.

*Primary Examiner*—June Hwu
*Assistant Examiner*—Louanne C Krawczewicz Myers
(74) *Attorney, Agent, or Firm*—C. A. Whealy

(57) ABSTRACT

A new and distinct cultivar of *Gerbera* plant named 'Redwood', characterized by its compact, upright and uniformly mounding plant habit; freely flowering habit; orange red-colored ray and disc florets; and upright, strong and relatively short scapes.

1 Drawing Sheet

Botanical designation: *Gerbera jamesonii.*
Cultivar denomination: 'REDWOOD'.

BACKGROUND OF THE INVENTION

The present invention relates to a new and distinct cultivar of *Gerbera* plant, botanically known as *Gerbera jamesonii* and hereinafter referred to by the name 'Redwood'.

The new *Gerbera* plant is a product of a planned breeding program conducted by the Inventor in De Kwakel, The Netherlands. The objective of the breeding program is to create new compact container *Gerbera* cultivars with numerous inflorescences, good garden performance and attractive inflorescence coloration.

The new *Gerbera* plant originated from a cross-pollination during the summer of 2005 in De Kwakel, The Netherlands of *Gerbera jamesonii* 'Flomountain', disclosed in U.S. Plant Pat. No. 21,340, as the female, or seed, parent *Gerbera jamesonii* 'Flopacific', disclosed in U.S. Plant patent application Ser. No. 12/454,018, as the male, or pollen, parent. The new *Gerbera* plant was discovered and selected by the Inventor as a single flowering plant within the progeny of the stated cross-pollination in a controlled greenhouse environment in De Kwakel, The Netherlands during the spring of 2006.

Asexual reproduction of the new *Gerbera* plant by tissue culture in a controlled environment in De Kwakel, The Netherlands since the summer of 2006 has shown that the unique features of this new *Gerbera* plant are stable and reproduced true to type in successive generations.

SUMMARY OF THE INVENTION

Plants of the new *Gerbera* have not been observed under all possible environmental conditions. The phenotype may vary somewhat with variations in environment such as temperature and light intensity, without, however, any variance in genotype.

The following traits have been repeatedly observed and are determined to be the unique characteristics of 'Redwood'. These characteristics in combination distinguish 'Redwood' as a new and distinct cultivar of *Gerbera:*

1. Compact, upright and uniformly mounding plant habit.
2. Freely flowering habit.
3. Orange red-colored ray and disc florets.
4. Upright, strong and relatively short scapes.

Plants of the new *Gerbera* differ from plants of the female parent, 'Flomountain', in the following characteristics:

1. Plants of the new *Gerbera* are broader than plants of 'Flomountain'.
2. Leaves of plants of the new *Gerbera* have more rounded apices than leaves of plants of 'Flomountain'.
3. Ray florets of plants of the new *Gerbera* are red orange in color whereas ray florets of plants of 'Flomountain' are light orange and orange in color.

Plants of the new *Gerbera* differ from plants of the male parent, 'Flopacific', in the following characteristics:

1. Plants of the new *Gerbera* have larger inflorescences than plants of 'Flopacific'.
2. Plants of the new *Gerbera* and 'Flopacific' differ in ray floret coloration as plants of 'Flopacific' have pink and red purple-colored ray florets.

Plants of the new *Gerbera* can be compared to plants of the *Gerbera jamesonii* 'Flomite', disclosed in U.S. Plant Pat. No. 21,309. Plants of the new *Gerbera* differ from plants of 'Flomite' in the following characteristics:

1. Plants of the new *Gerbera* are shorter than plants of 'Flomite'.
2. Plants of the new *Gerbera* have smaller inflorescences than plants of 'Flomite'.

BRIEF DESCRIPTION OF THE PHOTOGRAPH

The accompanying photograph illustrates the overall appearance of the new *Gerbera* plant. The photograph shows the colors as true as it is reasonably possible to obtain in colored reproductions of this type. Colors in the photograph may differ slightly from the color values cited in the detailed botanical description which accurately describe the colors of the new *Gerbera* plant. The photograph comprises a side perspective view of a typical flowering plant of 'Redwood' grown in a container.

DETAILED BOTANICAL DESCRIPTION

The aforementioned photograph and following observations and measurements describe plants grown in a glass-covered greenhouse during the spring and summer in De Kwakel, The Netherlands and under conditions and practices which approximate those generally used in commercial container *Gerbera* production. During the production of the plants, day temperatures ranged from 19° C. to 26° C. and night temperatures ranged from 16° C. to 18° C. Rooted young tissue-cultured plants were planted in 19-cm containers and were six months old when the photograph was taken and ten months old when the description was taken. In the following description, color references are made to The Royal Horticultural Society Colour Chart, Fifth Edition, 2007, except where general terms of ordinary dictionary significance are used.

Botanical classification: *Gerbera jamesonii* 'Redwood'.

Parentage:

*Female, or seed, parent.*—*Gerbera jamesonii* 'Flomountain', disclosed in U.S. Plant Pat. No. 21,340.

*Male, or pollen, parent.*—*Gerbera jamesonii* 'Flopacific', disclosed in U.S. Plant patent application Ser. No. 12/454,018.

Propagation:

*Type.*—By tissue culture.

*Time to initiate roots.*—About 2.5 weeks at temperatures of 20° C.

*Time to produce a rooted young plant.*—About five to six weeks at temperatures of 20° C. to 26° C.

*Root description.*—Fibrous; white in color.

*Rooting habit.*—Moderate branching; dense.

Plant description:

*Appearance.*—Herbaceous perennials with semi-double inflorescences that are typically grown as a container or garden plants; compact, upright and uniformly mounding plant habit; leaves arranged in basal rosettes and outwardly arching; dense and bushy habit; moderately vigorous growth habit.

*Plant height.*—About 43 cm.

*Plant width.*—About 80 cm.

Foliage description:

*Arrangement.*—Alternate, simple.

*Length.*—About 45 cm.

*Width.*—About 17 cm.

*Shape.*—Runcinate; lanceolate to narrowly elliptic in outline.

*Apex.*—Obtuse, rounded to abruptly acute.

*Base.*—Acuminate.

*Margin.*—Pinnately lobed with coarse and irregular sinuses, lobes divergent; undulate.

*Texture, upper surface.*—Sparsely pubescent.

*Texture, lower surface.*—Moderately pubescent; woolly.

*Venation pattern.*—Pinnate.

*Color.*—Developing leaves, upper surface: Close to 137A. Developing leaves, lower surface: Close to 138B. Fully expanded leaves, upper surface: Close to 141A; venation, close to 144B to 144C. Fully expanded leaves, lower surface: Close to 138B; venation, close to 144B.

*Petioles.*—Length: About 12 cm. Diameter: About 5.5 mm. Texture, upper surface: Sparsely pubescent. Texture, lower surface: Moderately pubescent. Color, upper and lower surfaces: Close to 144B.

Inflorescence description:

*Appearance.*—Semi-double type inflorescence form with narrowly obovate-shaped ray florets; solitary inflorescences borne on upright, strong and relatively short scapes above the foliar plane; ray and disc florets arranged acropetally on a capitulum.

*Fragrance.*—None detected.

*Flowering season.*—Plants begin flowering about four months after planting and flower from early spring to the end of the summer in outdoor gardens in The Netherlands; plants flower year-round under greenhouse conditions.

*Inflorescence longevity.*—Inflorescences last about two weeks on the plant; inflorescences persistent.

*Quantity of inflorescences.*—Freely flowering habit with about eight open and developing inflorescences per plant at one time.

*Inflorescence bud.*—Height: About 1.6 cm. Diameter: About 3.6 cm. Shape: Oblate. Color: Close to 144B; mid-section, close to 203D.

*Inflorescence size.*—Diameter: About 10.4 cm. Depth (height): About 2.3 cm. Diameter of disc: About 2.8 cm. Receptacle height: About 8 mm. Receptacle diameter: About 9 mm. Receptacle color: Close to NN155C.

*Ray florets.*—Orientation: Initially upright, then roughly perpendicular to the peduncle and slightly reflexing. Length: About 4.6 cm. Width: About 1.2 cm. Shape: Narrowly obovate. Apex: Obtuse, rounded. Base: Cuneate. Margin: Entire. Texture, upper and lower surfaces: Smooth, glabrous; longitudinally ridged. Number of ray florets per inflorescence: About 65 outer ray florets and about 400 inner ray florets arranged in about three whorls. Color: When opening, upper surface: Close to 40A. When opening, lower surface: Close to 1A. Fully opened, upper surface: Close to 33A. Fully opened, lower surface: Close to 7C.

*Disc florets.*—Arrangement: Massed at center of receptacle. Shape: Tubular, fused. Apex: Acute. Base: Fused. Margin: Entire. Length: About 1 cm. Width: About 4.5 mm. Texture, upper and lower surfaces: Smooth, glabrous. Number of disc florets per 202A. Color, mature: Apex, close to 32A; mid-section and base, close to 16D.

*Pappus.*—Quantity per floret: About 50. Length: About 8 mm. Diameter: Less than 1 mm. Texture: Soft. Color: Close to N77A and 187A.

*Phyllaries.*—Number of phyllaries per inflorescence: About 96 in about three whorls. Length: About 1 cm. Width: About 2 mm. Shape: Lanceolate. Apex: Acute. Base: Cuneate. Margin: Entire. Texture, upper surface: Smooth, glabrous. Texture, lower surface: Densely tomentose. Color, upper surface: Close to 138B. Color, lower surface: Close to 137B; towards the apex, close to 143B.

*Scapes.*—Length: About 43 cm. Diameter: About 8 mm. Angle: Erect. Strength: Strong. Texture: Densely tomentose. Color: Close to 144B; towards the apex, close to 137B.

*Reproductive organs.*—Androecium: Present on disc florets only. Quantity per floret: Two. Filament length: About 6 mm. Filament color: Close to NN155C.

Anther shape: Lanceolate. Anther length: About 4 mm. Anther color: Close to 12B. Pollen amount: Moderate. Pollen color: Close to 12A. Gynoecium: Present on disc florets only. Quantity per floret: One. Pistil length: About 1.1 cm. Stigma shape: Rounded; curved. Stigma color: Close to 155D. Style length: About 1 cm. Style color: Close to NN155C. Ovary color: Close to 145D.

*Seed/fruit.*—Seed and fruit production has not been observed.

Disease/pest resistance: Resistance to pathogens and pests common to *Gerberas* has not been observed on plants of the new *Gerbera* grown under commercial conditions.

Temperature tolerance: Plants of the new *Gerbera* have been observed to tolerate temperatures from about 1° C. to about 35° C.

It is claimed:

1. A new and distinct *Gerbera* plant named 'Redwood' as illustrated and described.

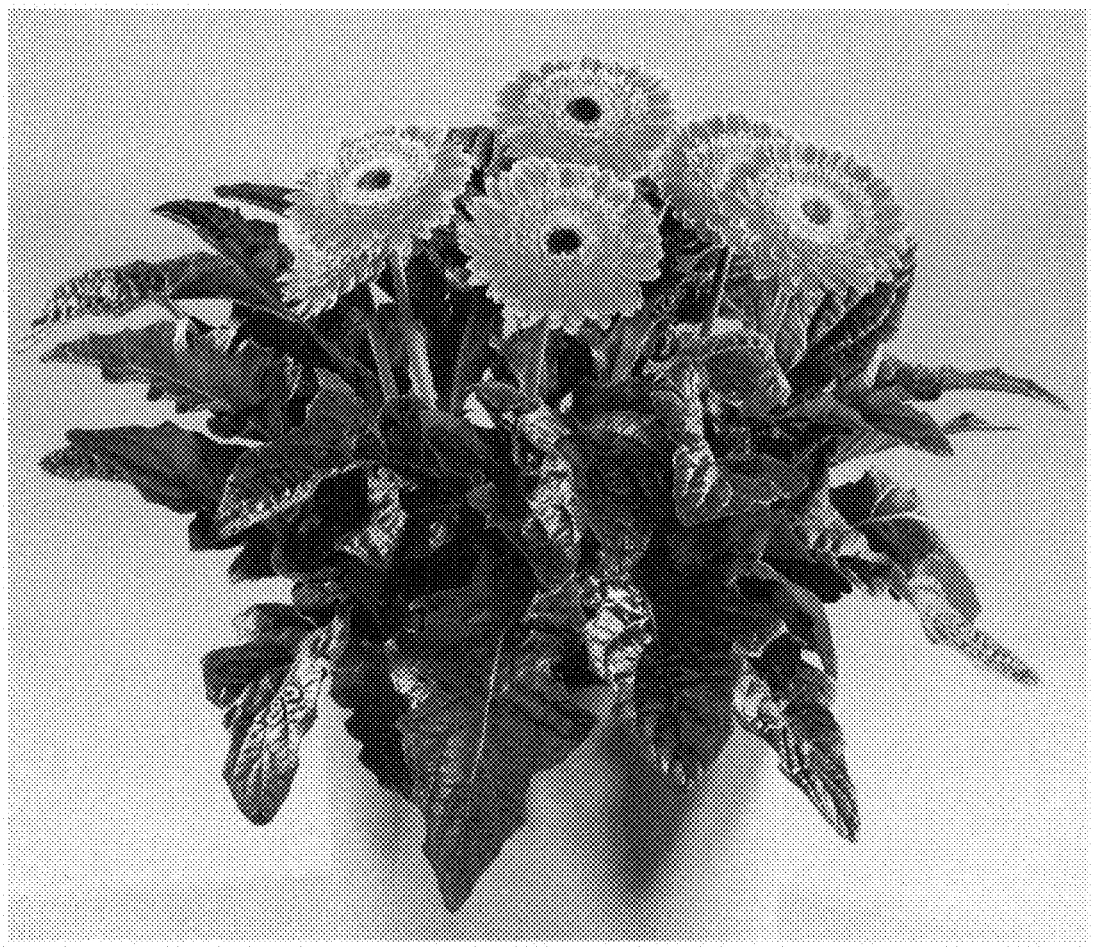

* * * * *